United States Patent [19]

Gless, Jr. et al.

[11] Patent Number: 5,565,608
[45] Date of Patent: Oct. 15, 1996

[54] PROCESS FOR THE PREPARATION OF 2-(SUBSTITUTED)-4-SULFOBENZOIC ACID

[75] Inventors: Richard D. Gless, Jr., Oakland; Nancy Kerlinger, Lafayette; Peter K. Wehrenberg, Piedmont, all of Calif.

[73] Assignee: Zeneca Limited, London, England

[21] Appl. No.: 479,426

[22] Filed: Jun. 7, 1995

[51] Int. Cl.$^6$ .................................................. C07C 309/29
[52] U.S. Cl. .................................................. 562/56; 562/57
[58] Field of Search .................................... 562/56, 57

[56] References Cited

U.S. PATENT DOCUMENTS 5,008,448  4/1991  Brown .
5,175,351  12/1992  Rohrscheid .
5,424,481  6/1995  Hagen .

FOREIGN PATENT DOCUMENTS

94/27959  12/1994  WIPO .

OTHER PUBLICATIONS

Y. Sasson et al., "Liquid Phase Oxidation of deactivated Methylbenzenes by Aqueous Sodium Hypochlorite Catalyzed by Ruthenium Salts under Phase–Transfer Catalytic Conditions" *J. Org. Chem.* 1986, 51, 2880–2883. Columbus, OH.

Nippon Kayaku Co., Ltd., "Sulfonitrobenzoic acids," Abstract of Jpn. Kokai Tokkyo Koho JP 57/200353 A2 [82/200353] Dec. 8, 1982., Japan.

*Primary Examiner*—Nicky Chan
*Attorney, Agent, or Firm*—Joseph R. Snyder

[57] ABSTRACT

A process for the preparation of 2-(substituted)-4-sulfobenzoic acid by oxidation of 2-(substituted)-4-toluenesulfonic acid.

4 Claims, No Drawings

PROCESS FOR THE PREPARATION OF 2-(SUBSTITUTED)-4-SULFOBENZOIC ACID

This invention relates to a process for the preparation of 2-(substituted)-4-sulfobenzoic acid by oxidation of 2-(substituted)-4-toluenesulfonic acid.

BACKGROUND OF THE INVENTION

Certain 2-(2'-substituted)benzoyl-1,3-cyclohexanedione herbicides are described in U.S. Pat. No. 4,946,981 and U.S. Pat. No. 5,006,158.

One preferred group of the above-described herbicidal compounds have the following formula

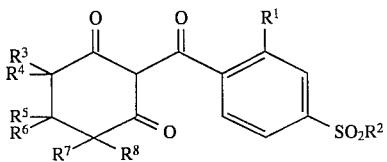

wherein $R^1$ is nitro, chloro or bromo; $R^2$ is hydrogen or $C_1$–$C_4$ alkyl; $R^3$ is hydrogen or $C_1$–$C_4$ alkyl; $R^4$ is hydrogen, $C_1$–$C_4$ alkyl or

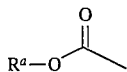

wherein $R^a$ is $C_1$–$C_4$ alkyl; or $R^3$ and $R^4$ together form an alkylene having 3–6 carbon atoms; and $R^5$, $R^6$, $R^7$, and $R^8$ are each independently hydrogen or $C_1$–$C_4$ alkyl.

These herbicides can be prepared by reacting a mole of dione having the structural formula

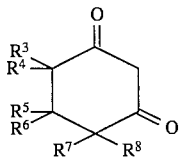

wherein $R^3$ through $R^8$ are as defined above with a mole of 2-(substituted)-4-(alkylsulfonyl)benzoyl chloride having the structural formula

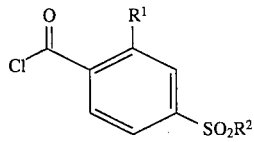

wherein $R^1$ is nitro, chloro or bromo and $R^2$ is hydrogen or $C_1$–$C_4$ alkyl.

A 2-(substituted)-4-(alkylsulfonyl)benzoyl chloride may be generated from its corresponding benzoic acid. It is possible to generate a benzoic acid from an alkyl-substituted benzene.

The oxidation of an alkyl-substituted benzene to its corresponding carboxylic acid (as shown in Scheme I) is a widely performed reaction and is known to occur by a variety of oxidants and under various reaction conditions.

SCHEME I

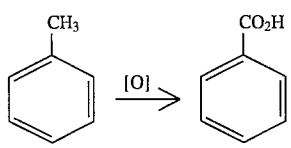

For instance, catalytic liquid-phase oxidations of toluenes are generally performed with molecular oxygen and catalytic amounts of cobalt acetate, manganese acetate and bromide ions in acetic acid as a solvent. This method is exemplified in U.S. Pat. No. 5,175,351, wherein alkanesulfonylalkylbenzenes are oxidized to alkanesulfonylbenzoic acids using molecular oxygen in acetic acid and/or propionic acid. The reaction is carried out in the presence of a catalyst containing cobalt and bromine ions and optionally also manganese ions and also magnesium and calcium ions. One disadvantage of that method is the requisite high pressure. For instance, Example 1 of that patent describes air being introduced at 16 bar pressure. This rigorous condition of high pressure is necessary to effectuate oxidation using this method.

In addition, EP 594,027 discloses the oxidation of ring-substituted alkyl benzenes to the corresponding carboxylic acids by the use of nitric acid as an oxidant. This reaction using nitric acid as an oxidant requires high temperatures (between 130° and 170° C.) and the use of a vanadium or cobalt catalyst.

*J. Org. Chem.* 1986, 51, 2880–2883, discloses the oxidation of ring-deactivated methylbenzenes to the corresponding carboxylic acids in a two phase (organic liquid/aqueous) system. The oxidation of the organic substrate is effected by aqueous sodium hypochlorite as primary oxidant in the presence of catalytic amounts of ruthenium tetraoxide ($RuO_4$). The $RuO_4$ is formed in situ by the action of sodium hypochlorite on $RuCl_3$. This procedure also requires the presence of a phase-transfer catalyst, in this case, a quaternary ammonium salt. Two phase systems are difficult to work with because vigorous stirring is required to obtain efficient and consistent reaction rates. Further, the introduction of a phase transfer catalyst is a limitation because of the possibility of forming emulsions upon workup. Use of two phases also decreases reaction volume; hence, there is a concomitant reduction in productivity. In addition, $RuCl_3$ is expensive and even if efficient recycle methods are developed, there are still considerable costs from lost ruthenium. Additional problems may also arise with ruthenium in the waste stream.

Japanese Patent Publication 57/200353 describes the oxidation of sulfonitrotoluenes with hypochlorites in the presence of a heavy metal peroxide and alkali hydroxides to generate sulfonitrobenzoic acids. The limiting aspects of this procedure are at least twofold. First, the presence of heavy metals (nickel) in the reaction mixture will require expensive disposal steps and second, the presence of peroxides may possibly lead to explosive mixtures.

It has now been surprisingly found that oxidation of 2-(substituted)-4-toluenesulfonic acids to the corresponding 2-(substituted)-4-sulfobenzoic acid by use of sodium hypochlorite may be accomplished without a metal catalyst and a phase transfer catalyst. Unexpectedly, the reaction can be carried out in a single aqueous phase. The fact that no additional catalysts are needed greatly reduces the costs of production and disposal of spent catalysts.

SUMMARY OF THE INVENTION

The present invention provides a process for preparing a 2-(substituted)-4-sulfobenzoic acid having the structural formula

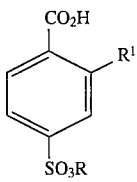

wherein $R^1$ is a nitro, chloro or bromo and R is hydrogen or an alkali metal. This process includes the steps of:

a) reacting a compound having the structural formula

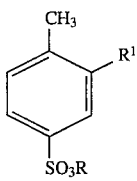

wherein R and $R^1$ are as described above, with sodium hypochlorite in the absence of a metal catalyst, heating the mixture to reflux; and then b) acidifying the mixture with an acid.

DETAILED DESCRIPTION OF THE INVENTION

This invention relates to a process for the preparation of 2-(substituted)-4-sulfobenzoic acid by oxidation of 2-(substituted)-4-toluenesulfonic acid. Especially preferred products of this invention are 2-chloro-4-sulfobenzoic acid and 2-nitro-4-sulfobenzoic acid. The inventive process can be represented schematically as follows:

SCHEME II

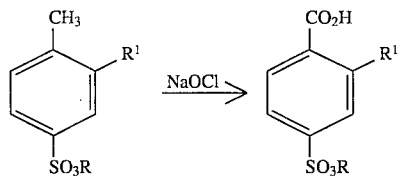

wherein $R^1$ is nitro, chloro or bromo and R is either hydrogen or an alkali metal. Preferably, $R^1$ is nitro or chloro and R is hydrogen, sodium or potassium.

Sodium hypochlorite is reacted in at least a molar excess amount compared to the 2-(substituted)- 4-toluenesulfonic acid. Preferably, at least a 2 molar excess of sodium hypochlorite is used compared to the 2-(substituted)-4-toluenesulfonic acid. Most preferably, a 3–4 molar excess of sodium hypochlorite is used compared to the 2-(substituted)-4-toluenesulfonic acid. The sodium hypochlorite may be from a commercially available source, or may be generated in situ by addition of chlorine and an alkaline solution.

The oxidation may suitably be performed at moderate temperatures (between 50° C. and 150° C.) and preferably run at reflux temperatures of 100°–105° C. The reaction mixture is refluxed for about 1 hour. The reaction may be monitored by an analytical technique such as nuclear magnetic resonance spectroscopy, to facilitate indication of a completed reaction. The mixture is then cooled and filtered. The filtrate is acidified with hydrochloric acid, or another suitable protic acid. Other suitable acids include hydrobromic, hydroiodic, sulfuric, and phosphoric acids. The preferred acid is hydrochloric acid. The desired product namely, 2-(substituted)-4-sulfobenzoic acid, precipitates upon acidification. Acid is added until no further precipitation occurs.

The following non-limiting example illustrates the instant invention:

EXAMPLE

To a 50 mL, three-neck round bottom flask was added 2.0 g (8.4 mmol) of 2-(nitro)-4-toluenesulfonic acid, 20 mL (32.2 mmol) of sodium hypochlorite and the reaction mixture was heated to reflux. After approximately an hour of reflux, the reaction mixture was cooled to room temperature and the reaction mixture was filtered. The filtrate was acidified with concentrated hydrochloric acid. A solid formed upon acidification, and acid was added until no further precipitation occurred. The solution was filtered and the solid collected. The solid 2-(nitro)- 4-sulfobenzoic acid product was dried and weighed. The yield was about 92%. The product was characterized by mass spectrometry and nuclear magnetic resonance spectroscopy.

Although the invention has been described with reference to the preferred embodiment and example thereof, the scope of the present invention is not limited only to the described embodiment. As will be apparent to persons skilled in the art, modifications and adaptations to the above described invention can be made without departing from the spirit and scope of the invention, which is defined and circumscribed by the appended claims.

What is claimed is:

1. A process for preparing a 2-(substituted)-4-sulfobenzoic acid having the structural formula

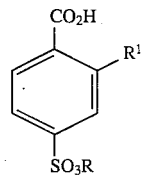

wherein $R^1$ is a member selected from the group consisting of nitro, chloro and bromo and R is hydrogen or an alkali metal, comprising the steps of:

a) reacting a compound having the following structural formula

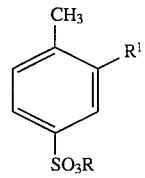

wherein R and $R^1$ are as described above, with at least a molar excess of sodium hypochlorite in the absence of a catalyst, heating the mixture to reflux; and b) acidifying with acid.

2. A process according to claim 1 wherein $R^1$ is chloro.

3. A process according to claim 1 wherein $R^1$ is nitro.

4. A process according to claim 1 wherein R is sodium or potassium.

* * * * *